(12) United States Patent
Asiedu et al.

(10) Patent No.: US 7,749,544 B2
(45) Date of Patent: Jul. 6, 2010

(54) COMPOSITION FOR TREATING AIDS AND ASSOCIATED CONDITIONS

(76) Inventors: William Asiedu, H/N B 183/19 Bintu Area, PMB Ministries, Accra (GH); Frederick Asiedu, H/N B 183/19 Bintu Area, PMB Ministries, Accra (GH); Manny Ennin, H/N B 183/19 Bintu Area, PMB Ministries, Accra (GH); Michael Nsiah Doudu, H/N B 183/19 Bintu Area, PMB Ministries, Accra (GH); Charles Antwi Boateng, H/N B 183/19 Bintu Area, PMB Ministries, Accra (GH); Kwasi Appiah-Kubi, H/N B 183/19 Bintu Area, PMB Ministries, Accra (GH); Seth Opoku Ware, H/N B 183/19 Bintu Area, PMB Ministries, Accra (GH); Debrah Boateng, H/N B 183/19 Bintu Area, PMB Ministries, Accra (GH); Kofi Ampim, 2 Kakramadu Ling, P.O. Box CT 245, Cantonments, PMB Ministries, Accra (GH); William Owusu, H/N B 183/19 Bintu Area, PMB Ministries, Accra (GH); Akwete Lex Adjei, 15 Tillman Ct., Bridgewater, NJ (US) 08807

( * ) Notice: Subject to any disclaimer, the term of this patent is extended or adjusted under 35 U.S.C. 154(b) by 0 days.

(21) Appl. No.: 10/902,993

(22) Filed: Jul. 30, 2004

(65) Prior Publication Data

US 2005/0181077 A1 Aug. 18, 2005

Related U.S. Application Data

(63) Continuation of application No. 10/241,973, filed on Sep. 12, 2002, now abandoned.

(51) Int. Cl.
A61K 36/00 (2006.01)
(52) U.S. Cl. .................................... 424/725
(58) Field of Classification Search .................... None
See application file for complete search history.

(56) References Cited

OTHER PUBLICATIONS

Calderon et al. (Phytotherapy Research (1997), vol. 11, pp. 606-608).*
Ojewole (International Journal of Crude Drug Research (1984), vol. 22, No. 3, pp. 121-143).*
Ginsberg and Spigelman (Nature Medicine (2007), vol. 13, No. 3, pp. 290-294).*
Engler and Prantl, *Die Naturlichen: Pflanzenfamilien*, 1897, p. 349.
Breteler, F .J. "Novitates Gabonenses 47. Another new *Dichapetalum* (Dichapetalaceae) from Gabon" *Adansonia*, 2003; 25(2) :223-227.
Fedkam Boyom et al. "Aromatic plants of tropical central Africa. Part XLIII: volatile components from *Uvariastrum pierreanum* Engl. (Engl. & Diels) growing in Cameroon" *Flavour and Fragrance Journal*, 2003; 18:269-298.

\* cited by examiner

*Primary Examiner*—Susan C Hoffman
(74) *Attorney, Agent, or Firm*—Frommer Lawrence & Haug LLP; Marilyn Matthes Brogan; Heather J. DiPietrantonio

(57) ABSTRACT

An Aids and associated conditions related to Aids treating compositions is disclosed. The compositions comprise: a medicament selected from an extract of at least one of the following plant families: Apocynaceae (*Pleioscarpa Bicarpellata*); Annonaceae (*Cleistopholis Patens*); Dichapetalaceae (*Dichapetehan Madagasca Riense*); Annoceae (*Uvaristrum Pierreanum*); Cynocynaceae (*Strophantus Gratus*); Asclepiadaceae (*Gongronema Latifolium*); Combretaceae (*Combretum Racemosum*); Apocynaceae (*Alostonia Boonei*); Amaranthaceae (*Alternanthera Pungens*); Aroceae (*Anchomanes Differmis*); Cyperaceae (*Seleria Voivinil*); Anacardiaceae (*Lannea Acida*); Bignoniaceae (*Kigelia Africana*); Bombacaceae (*Ceiba Pentanota*); Anarcardiaceae (*Antrocaryon Micraster*); Bombacaceae (*Bombax Bounopozense*): Anarcardiaceae (*Spondias Mombin*); Caricaceae (*Carica Papaya*); a glyceryl ester of any of the foregoing extracts; a saponin of any of the foregoing extracts; an alkaloid of any of the foregoing extracts; a protein of any of the foregoing extracts; a fat of any of the foregoing extracts; a sugar of any of the foregoing extracts; and any mixture of any of the foregoing.

3 Claims, No Drawings

COMPOSITION FOR TREATING AIDS AND ASSOCIATED CONDITIONS

This application is a continuation of U.S. application Ser. No. 10/241,973, filed Sep. 12, 2002, now abandoned.

BACKGROUND OF THE INVENTION

1. Field of the Invention

This invention relates to a composition for treating AIDS and related conditions, and more particular, to a composition comprising at least one extract of a selected plant.

2. Description of the Prior Art

Patients with illnesses that, in retrospect, were manifestations of acquired immunodeficiency syndrome (AIDS) were first described in the summer of 1981 [CDC—*Pneumocystis pneumonia*—Los Angeles. MMWR 1981, 30:250-2; CDC—*Kaposi's sarcoma and Pneumocystis pneumonia among homosexual men*—New York City and California. MMWR 1981, 30:305-8]. A case definition of AIDS for national reporting was first published in the MMWR in September 1982 [CDC—*Hepatitis B virus vaccine safety: report of an inter-agency group* MMWR 1982, 31:465-67; CDC—*Update on acquired immune deficiency syndrome (AIDS)—United States*. MMWR 1982, 31:507-14]. Since then the definition has undergone minor revisions in the list of diseases used as indicators of underlying cellular immunodeficiency [Jaffe H W, Bregman D J, Selik R M. *Acquired immune deficiency syndrome in the United States: the first 1,000 cases*. J Infect Dis 1983, 148:339-45; Jaffe H W, Selik R M. *Acquired immune deficiency syndrome: is disseminated aspergillosis predictive of underlying cellular immune deficiency?*, (Reply to letter), J Infect Dis 1984, 149:829; Selik R M, Haverkos H W, Curran J W. *Acquired immune deficiency syndrome (AIDS) trends in the United States, 1978-1982*. Am J Med 1984, 76:493-500; CDC, Update: acquired immunodeficiency syndrome (AIDS)—United States. MMWR 1984, 32:688-91]

Since the 1982 definition was published, human T-cell lymphotropic virus type III/lymphadenopathy-associated virus (HTLV-III/LAV) has been recognized as the cause of AIDS. The clinical manifestations of (HTLV-III/LAV) infection may be directly attributable to infection with this virus or the result of secondary conditions occurring as a consequence of immune dysfunction caused by the underlying infection with (HTLV-III/LAV). The range of manifestations may include none, nonspecific signs and symptoms of illness, autoimmune and neurologic disorders, a variety of opportunistic infections, and several types of malignacy. AIDS was defined for national reporting before its etiology was known and has encompassed only certain secondary conditions that reliably reflected the presence of a sever immune dysfunction. Current laboratory tests to detect (HTLV-III/LAV) antibody make it possible to include additional serious conditions in the syndrome, as well as to further improve the specificity of the definition used for reporting cases.

The current case definition of AIDS has provided useful data on disease trends, because it is precise, consistently interpreted, and highly specific. Other manifestations of HTLV-III/LAV infections than those currently proposed to be reported are less specific and less likely to be consistently reported nationally. Milder disease associated with HTLV-III/LAV infections and asymptomatic infections may be reportable in some states and cities but will not be nationally reportable. Because persons with less specific or milder manifestations of HTLV-III/LAV infection may be important in transmitting the virus, estimates of the number of such persons are of value. These estimates can be obtained through epidemiologic studies or special surveys in specific populations.

Issues related to the case definition of AIDS were discussed by the Conference of State and Territorial Epidemiologists (CSTE) at its annual meeting in Madison, Wis., Jun. 2-5, 1985. The CSTE approved the following resolutions:

1. that the case definition of AIDS used for national reporting continue to include only the more severe manifestations of HTLV-III/LAV infection; and
2. that the Center For Disease Control (CDC) develop more inclusive definitions and classifications of HTLV-III/LAV infection for diagnosis, treatment, and prevention, as well as for epidemiologic studies and special surveys; and
3. that the following refinements be adopted in the case definition of AIDS used for national reporting:
    a. In the absence of the opportunistic diseases required by the current case definition, any of the following diseases will be considered indicative of AIDS if the patient has a positive serologic or virologic test for HTLV-III/LAV:
1. disseminated histoplasmosis (not confined to lungs or lymph nodes), diagnosed by culture, histology, or antigen detection;
2. isosporiasis, causing chronic diarrhea (over 1 month), diagnosed by histology or stool microscopy;
3. bronchial or pulmonary candidiasis, diagnosed by microscopy or by presence of characteristic white plaques grossly on the bronchial mucosa (not by culture alone);
4. non-Hodgkins' lymphoma of high-grade pathologic type (diffuse, undifferentiated) and of B-cell unknown immunologic phenotype, diagnosed by biopsy;
5. histologically confirmed Kaposi's sarcoma in patients who are 60 years old or older when diagnosed.
    b. In the absence of the opportunistic diseases required by the current case definition, a histologically confirmed diagnosis of chronic lymphoid interstitial pneumonitis in a child (under 13 years of age) will be considered indicative of AIDS unless test(s) for HTLV-III/LAV are negative.
    c. Patients who have a lymphoreticular malignancy diagnosed more than 3 months after the diagnosis of an opportunistic disease used as a marker for AIDS will no longer be excluded as AIDS cases.
    d. To increase the specificity of the case definition, patients will be excluded as AIDS cases if they have a negative result on testing for serum antibody to HTLV-III/LAV, have no other type of HTLV-III/LAV test with a positive result, and do not have a low number of T-helper lymphocytes or a low ratio of T-helper to T-suppressor lymphocytes. In the absence of test results, patients satisfying all other criteria in the definition will continue to be included. CDC will immediately adopt the above amendments to the case definition of AIDS for national reporting.

This revision, in the case definition will result in the reclassification of less than 1% of cases previously reported to CDC. The number of additional new cases reportable as a result of the revision is expected to be small. Cases included under the revised definition will be distinguishable from cases included under the old definition so as to provide a consistent basis for interpretation of trends. CDC will also develop draft classifications for disease manifestations of HTLV-III/LAV infections other than AIDS, distribute these widely for comment, and publish the results. Reported by Conference of State and Territorial Epidemiologists; AIDS Br., Div of Viral Diseases, Center for Infectious Disease, CDC.

Han et al. Disclosed a process for preparing an extracted substance from, a mixture of a non-fat starch from Ricini Semen and a root of Coptis sp for therapeutic applications of AIDS [U.S. Pat. No. 5,928,645]. The authors maintain that the extracted substance was effective in treating AIDS but provided no clinical data as to the effect of this substance in AIDS patients. In continuing work, Han et al., demonstrated significant anti-oxidant capacity of their Ricini Semen extract using a chemiluminescence assay [Hong, E. K., Kim, Y. K. Lee, W. C., Shin, H. K., and Kim, J. B.; Measurement of antioxidation activity based on chemiluminescence reaction. In Bioluminescence and Chemiluminescence (Status Report), Eds. Szalay, A. A., Kricka, L. J., and Stanley, P., John Wiley & Sons Ltd. London, England, pp. 244-246, 1993]. Antioxidant activity of Ricini Semen extract was compared with t-butylhydroxy toluene (BHT), a potent antioxidant known to people of ordinary skill in the field of the invention. The authors therefore proposed that Ricini Semen extract has anti-HIV effect although no clinical data was presented. Investigations of the Ricini Semen extract in laboratory animals by sub-cutaneous injection revealed significant tubular necrosis, glomerulonephritis, and vacuolation in livers of male and female mice, interstitial nephritis being demonstrated as well in female mice. Rats showed similar symptoms in both of the male and female. Mitosis in the liver was typically found, and extramedullary hematopoiesis in the liver and spleen also were frequently observed. Other organs were not changed compared to controls [U.S. Pat. No. 5,928,645].

Chen et al., [U.S. Pat. No. 6,077,512] disclosed a novel topical treatment method for curing black foot disease using plant extracts. The extract medicament comprised a basis part consisting of equal amounts of ground, powdered, and mixed clove, frankincense, myrrha, fhizama arisaematis, pinellia, monkshood (root) or kusnezoff monkshood (root), and tuber of bamboo-leaved orchid, and an adjuvant part consisting of equal amounts of round, powdered, and mixed borneol, powdered soy bean, borax, coptis root and/or phellodendron amureause, and sepia aculeata. The medicine is used in such a manner that the powdered basis part is mixed and stirred with tea water until it becomes plaster-like, and the adjuvant part is scattered in dry form onto the wound or swollen area caused by the black foot disease before the plaster-like basis part is applied to the wound or swollen area about 0.5 cm in thickness. The wound is then bandaged and the medicine is renewed once or twice a day until fresh flesh appears in the wound. Thereafter, the medicine is continuously applied but in a dry form until the wound is completely healed. The extract medicament composition taught by Chen et al., does not have any impact on AIDS itself as a systemic disease.

SUMMARY OF THE INVENTION

The present invention is related to a composition for treating AIDS and associated conditions related to AIDS the composition comprises a medicament which is an extract of at least one plant family.

DETAILED DESCRIPTION

The present invention relates to a novel extract medicament for use in treating AIDS, an immune deficiency or immunologically compromised disease, as well as a variety of AIDS related ailments, including recurrent and persistent fever, chronic diarrhea, dermatitis, generalized lymphodenpathy, persistent cough, general pain, tuberculosis, and amenorrhea. The extract is prepared from the bark, leaf, root and stems of at least one plant from within the apocynaceae, annonaceae, dichapetalaceae, annoceae, cynocynaceae, asclepiadaceae, combretaceae, amaranthaceae, araceae, cyperaceae, anacardiaceae, bignoniaceae, bombacaceae, and caricacea plant families.

A suitable plant is selected. Preferably a mixture of at least two plants is selected. Suitable plants are selected from a family of plants including (1) apocynaceae, (2) annonaceae, (3) dichapetalaceae, (4) annoceae, (5) cynocynaceae, (6) asclepiadaceae, (7) combretaceae, (8) amaranthaceae, (9) araceae, (10) cyperaceae, (11) anacardiaceae, (12) bignoniaceae, (13) bombacaceae, (14) an arcardiaceae and caricaceae plant families.

These plants are tropical herbs that grow naturally and can be thus cultivated in tropical, savanna, grassland or lightly wooded forests of West Africa. These desert plants can also be found in other tropical regions of the world, including Asia, Asia Minor, South America and possibly the South-Western, Western and Plains regions of the United States. The active medicaments from these plants include, but are not limited to glyceryl esters, saponins and several derivatives of alkaloids, glycosides, proteins, fats, and sugars.

The plants per se are not employed as the requisite medicament, but rather the extract of such selected plant or plants. The extraction process for the medicaments from the respective plants comprises the following:

(a) harvesting the barks, stems, leaves and roots of each plant, and cutting these into chips and chunks;

(b) washing and drying the chips and chunks under a controlled temperature condition, typically about 15° to 68° C. for about 3 days;

(c) proportionally mixing the washed and dried materials from each plant to formulate a mixture needed for each type of clinical application;

(d) grinding the resultant mixture of plant parts to a powder composition having a particle size typically ranging in size from about 100 microns to about 10,000 microns;

(e) extracting about one part of the resultant powdery mixture in about two parts of purified water under slow percolation for about 1 to about 5 hours under a temperature in the range of about 76° to about 116° C. and allowing the mixture to cool in appropriate containers under ambient temperature conditions, i.e., about 16° to about 33° C., for approximately 1 to 2 days;

(f) re-extracting the resultant mixture in a second percolation process using approximately 2 parts of purified water under slow percolation for about 1 to about 5 hours under a temperature in the range of about 76° to about 116° C. and allowing the mixture to cool in appropriate containers under ambient temperature conditions i.e., about 16° to about 33° C., for approximately 1 to 2 days;

(g) repeating the extraction process a third time using a double portion of purified water under slow percolation for about 1 to about 5 hours under a temperature in the range of about 76° to about 116° C. and allowing the mixture to cool in appropriate containers under ambient temperature conditions i.e., about 16° to about 33° C., for approximately 1 to 2 days;

(h) adding a conventional preservative system, e.g., cresols, parabens, p-chlormoetaxylenol, benzoates, alcohols, to maintain antimicrobial preservative efficacy of the mixed plant extract;

(i) mixing the extracts in a suitable container, and subjecting the resulting elute repeatedly to filtration under appropriate pressure and temperature conditions, to yield a pure, clean, preserved plant extract for human consumption;

(j) fill the resultant extract through a stainless steel strainer into appropriate containers for distribution; and (k) labeling the containers and presenting these for storage (The resultant concentrate may also be further concentrated into powder under reduced temperature/pressure conditions, e.g, by tray drying, solvent extraction, solvent exclusion, or spray drying, to result in a yellowish-brown amporphous, powder for use as an injectable or solid product such as a tablet; or by subjecting the resultant product to a filtration through a membrane filter and then a lypohilization to give powders; and then packaging the resulting mixed extracts in appropriate closure systems for clinical use.

Typically the resultant concentrated extract contains the following compounds for each plant concentrate obtained: [see L. Watson and M. J. Dallwitz (1992) onwards). The Families of Flowering Plants: Descriptions, Illustrations, Identification, and Information Retrieval. Version: 14 Dec. 2000]:

TABLE I

| PLANT | COMPOUNDS |
|---|---|
| (1) Apocynaceae | |
| Taxonomy: Subclass Dicotyledonae; Tenuinucelli. Dahlgren's Superorder Gentianiflorae. Species 1500. Genera 164; *Acokanthera, Adenium, Aganonerion, Aganosma, Alafia, Allamanda, Allomarkgrafia, Allowoodsonia, Alstonia, Alyxia, Amocalyx, Ambelania, Amsonia, Ancylobotrys, Anechites, Angadenia, Anodendron, Apocynum, Arduina, Artia, Asketanthera, Aspidosperma, Baissea, Beaumontia, Bousigonia, Cabucala, Callichilia, Calocrater, Cameraria, Carissa, Carpodinus, Carruthersia, Carvalhoa, Catharanthus, Cerbera, Cerberiopsis, Chamaeclitandra, Chilocarpus, Chonemorpha, Cleghornia, Clitandra, Condylocarpon, Couma, Craspidospermum, Crioceras, Cycladenia, Cyclocotyla, Cylindropsis, Delphyodon, Dewevrella, Dictyophleba, Dipladenia, Diplorhynchus, Dyera, Ecdysanthera, Echites, Elytropus, Epigynium, Eucorymbia, Farquharia, Fernaldia, Forsteronia, Funtumia, Galactophora, Geissospermum, Gonioma, Grisseea, Hancornia, Haplophyton, Himatanthus, Holarrhena, Hunteria, Hymenolophus, Ichnocarpus, Isonema, Ixodonerium, Kamettia, Kibatalia, Kopsia, Lacmellea, Landolphia, Laubertia, Laxoplumeria, Lepinia, Lepiniopsis, Leuconotis, Lochnera, Lyonsia, Macoubea, Macropharynx, Macrosiphonia, Malouetia, Mandevilla, Mascarenhasia, Melodinus, Mesechites, Micrechtites, Microplumeria, Molongum, Mortoniella, Motandra, Mucoa, Neobracea, Neocouma, Nerium, Nouettea, Ochrosia, Odontadenia, Orthopichonia Oncinotis, Pachypodium, Pachouria, Papuechites, Parahancornia, Parameria, Parepigynum, Parsonsia, Peltastes, Pentalinon, Petchia, Picralima, Plectaneia, Pleiocarpa, Pleioceras, Plumeria, Pottsia, Prestonia, Pycnobotrya, Quiotania, Rauwolfia, Rhabdadenia, Rhazya, Rhigospira, Rhodocalyx, Rhyncodia, Saba, Salpinctes, Schizozygia, Secondatia, Sindechites, Spongiosperma Skytanthus, Spirolobium, Stemmadenia, Stephanostegia, Stephanostema, Stipecoma, Strempeliopsis, Strophanthus, Tabernaemontana, Tabernanthe, Temnadenia, Thenardia, Thevetia, Tintinnabularia, Trachelospermum, Urceola, Urnularia, Vahadenia, Vallariopsis, Vallaris, Vallesia, Vinca, Voacanga, Willughbeia, Woytkowskia, Wrightia, Xylinabaria, Xylinabariopsis.* | cyanogenics, alkaloids iridoids verbascosides, proanthocyanidins, cyanidins delphinidins, flavonols, kaempferols, quercetins, ellagic acid, ursolic acid, saponins/sapogenins, aluminum salts, sucrose, oligosaccharides, and sugar alcohols |
| (2) Annonaceae | |
| Taxonomy - Subclass Dicotyledonae; Crassinucelli. Dahlgren's Superorder Magnoliiflorae; Annonales. Cronquist's Subclass Magnoliidae; Magnoliales. APG (1998) basal order; Magnoliales. Species 1200. Genera 126; *Afroguatteria, Alphonsea, Ambavia, Anaxagorea, Ancana, Annickia, Annona, Anomianthus, Anonidium, Artabotrys, Asimina, Asteranthe, Balonga, Bocagea, Bocageopsis, Boutiquea, Cananga, Cardiopetalum, Chieniodendron, Cleistochlamys, Cleistopholis, Cremastosperma, Cyathocalyx, Cyathostemma, Cymbopetalum, Dasoclema, Dasymaschalon, Deeringothamnus, Dendrokingstonia, Dennettia, Desmopsis, Desmos, Diclinanona, Dielsiothamnus, Disepalum, Duckeanthus, Duguetia, Ellipeia, Ellipeiopsis, Enicosanthum, Ephedranthus, Exellia, Fissistigma, Fitzalania, Friesodielsia, Froesiodendron, Fusaea, Gilbertiella, Goniothalamus, Greenwayodendron, Guamia, Guatteria, Guatteriella,* | cyanogenics, alkaloids, iridoids, proanthocyanidins, cyanidin, flavonols, quercetins, ellagic acid, sucrose, oligosaccharides |

TABLE I-continued

| PLANT | COMPOUNDS |
|---|---|
| *Guatteriopsis, Haplostichanthus, Heteropetalum, Hexalobus, Hornschuchia, Isolona, Letestudoxa, Lettowianthus, Malmea, Marsypopetalum, Meiocarpidium, Meiogyne, Melodorum, Mezzettia, Mezzettiopsis, Miliusa, Mischogyne, Mitrella, Mitrephora, Mkilua, Monanthotaxis, Monocarpia, Monocyclanthus, Monodora, Neostenanthera, Neo-uvaria, Oncodostigma, Onychopetalum, Ophrypetalum, Oreomitra, Orophea, Oxandra, Pachypodanthium, Papualthia, Petalolophus, Phaeanthus, Phoenicanthus, Piptostigma, Platymitra, Polyalthia, Polyaulax, Polyceratocarpus, Popowia, Porcelia, Pseudartabotrys, Pseudephedranthus, Pseudoxandra, Pseuduvaria, Pyramidanthe, Raimondia, Reedrollinsia, Richella, Rollinia, Ruizodendron, Sageraea, Sapranthus, Schefferomitra, Sphaerocoryne, Stelechocarpus, Stenanona, Tetrameranthus, Tetrapetalum, Toussaintia, Tridimeris, Trigynaea, Trivalvaria, Unonopsis, Uvaria, Uvariastrum, Uvariodendron, Uvariopsis, Woodiellantha, Xylopia.*<br>(3) dichapetalaceae | |
| Taxonomy. Subclass Dicotyledonae; Crassinucelli. Dahlgren's Superorder Malviflorae; Euphorbiales. Cronquist's Subclass Rosidae; Celastrales. APG (1998) Eudicot; core Eudicot; Rosid; Eurosid I; Malpighiales. Species 200. Genera 3; *Dichapetalum, Stephanopodium, Tapura, (Gonypetalum, Falya)*<br>(4) Annoceae | alkaloids, saponins, aluminium salts, oligosaccharides, sucrose |
| *Schefferomitra subaequalis, Goniothalamus sesquipedalis Uvariastrum*<br><br><br><br><br><br>(5) Cynosuraceae | Alkaloids, cyanidins,<br><br>flavonols, eg. kaempferol, quercetin, and myricetin; saponins/sapogenins sugars as sucrose, oligosaccharides or sugar alcohols |
| *Aegilopaceae, Agrostidaceae, Alopecuraceae, Andropogonaceae, Anomochloaceae, Anthoxanthaceae, Arundinaceae, ArundinellaceaeAsperellaceae, Avenaceae Bambusaceae, Chaeturaceae, Chloridaceae, Coleanthaceae Cynosuraceae, Echinariaceae, Ehrhartiaceae, Eragrostidaceae, Festucaceae, Glyceriaceae, Gramineae Hordeaceae, Lepturaceae, Maydaceae, Melicaceae, Miliaceae, Nardaceae, Oryzaceae, Panicaceae, Pappophoraceae, Paspalaceae, Parianaceae, Phalaridaceae, Pharaceae, Saccharaceae, Spartinaceae, Sporobolaceae, Stipaceae, Streptochaetaceae, Tristeginaceae, Triticaceae, Zeaceae*<br>(6) Asclepiadacea | alkaloids, arthroquinones, proanthocyanidins, cyanidins, flavonols, kaempferol, quercetin, myricetin, ellagic acid, aluminium, sucrose and oligosaccharides |
| Taxonomy. Subclass Dicotyledonae; Tenuinucelli. Dahlgren's Superorder Gentianiflorae; Gentianales. Cronquist's Subclass Asteridae; Gentianales. APG (1998) Eudicot; core Eudicot; Asterid; Euasterid I; Gentianales (as a synonym of *Apocynaceae*). Species 2000. Genera 250; *Absolmsia, Adelostemma, Aidomene, Amblyopetalum, Amblystigma, Anatropanthus, Anisopus, Anisotoma, Anomotassa, Araujia, Asclepias, Aspidoglossum, Astephanus, Barjonia, Belostemma, Bidaria, Biondia, Blepharodon, Blyttia, Brachystelma, Calotropis, Campestigma, Caralluma, Ceropegia, Cibirhiza, Cionura, Clemensiella, Conomitra, Cordylogyne, Corollonema, Cosmostigma, Costantina, Cyathostelma, Cynanchum, Dactylostelma, Dalzielia, Decabelone, Decanema, Decanemopsis, Dicarpophora, Diplolepis, Diplostigma, Dischidanthus, Dischidia, Ditassa, Dittoceras, Dolichopetalum, Dolichostegia, Dorystephania, Dregea, Drepanostemma, Duvalia, Duvaliandra, Echidnopsis, Edithcolea, Emicocarpus, Emplectranthus, Eustegia, Fanninia, Fischeria, Fockea, Folotsia, Frerea, Funastrum, Genianthus, Glossonema, Glossostelma, Gomphocarpus, Gongronema, Gonioanthelma, Goniostemma, Gonolobus, Graphistemma, Gunnessia, Gymnema, Gymnemopsis, Harmandiella, Hemipogon, Heterostemma, Heynella, Hickenia, Holostemma, Hoodia, X-Hoodiopsis, Hoya, Hoyella, Huernia, Huerniopsis, Hypolobus, Ischnostemma,* | alkaloids, hydrocitric acid, L-carnitine, 3B glucuronides of different acetylated gymnemagenins, gymnemic acid a complex mixture of at least 9 closely related acidic glucosides, flavonols including kaempferol, kaempferol and quercetin, aluminium, sucrose and oligosaccharides, iridoids. |

TABLE I-continued

| PLANT | COMPOUNDS |
|---|---|
| *Jacaima, Janakia, Jobinia, Kanahia, Karimbolea, Curb, Labidostelma, Lagoa, Lavrania, Leichardtia, Leptadenia, Lhotzkyella, Lugonia, Lygisma, Macroditassa, Macropetalum, Macroscepis, Mahafalia, Mahawoa, Manothrix, Margaretta, Marsdenia, Matelea, Melinia, Meresaldia, Merrillanthus, Metaplexis, Metastelma, Micholitzea, Microdactylon, Microloma, Microstelma, Miraglossum, Mitostigma, Morrenia, Nautonia, Nematostemma, Neoschumannia, Nephradenia, Notechidnopsis, Odontanthera, Odontostelma, Oncinema, Oncostemma, Ophionella, Orbea, Orbeanthus, Orbeopsis, Oreosparte, Orthanthera, Orthosia, Oxypetalum, Pachycarpus, Pachycymbium, Papuastelma, Parapodium, Pectinaria, Pentabothra, Pentacyphus, Pentarrhinum, Pentasachme, Pentastelma, Pentatropis, Peplonia, Pergularia, Periglossum, Petalostelma, Petopentia, Pherotrichis, Piaranthus, Platykeleba, Pleurostelma, Podandra, Podostelma, Prosopostelma, Pseudolithos, Ptycanthera, Pycnoneurum, Pycnorhachis, Quaqua, Quisumbingia, Raphistemma, Rhyncharrhena, Rhynchostigma, Rhyssolobium, Rhyssostelma, Rhytidocaulon, Riocreuxia, Rojasia, Sarcolobus, Sarcostemma, Schistogyne, Schistonema, Schizoglossum, Schubertia, Scyphostelma, Secamone, Secamonopsis, Seshagiria, Sisyranthus, Solenostemma, Sphaerocodon, Spirella, Stapelia, Stapelianthus, Stapeliopsis, Stathmostelma, Steleostemma, Stelmagonum, Stelmatocodon, Stenomeria, Stenostelma, Stigmatorhynchus, Strobopetalum, Stuckertia, Swynnertonia, Tassadia, Tavaresia, Telminostelma, Telosma, Tenaris, Tetracustelma, Tetraphysa, Thozetia, Toxocarpus, Treutlera, Trichocaulon, Trichosacme, Trichosandra, Tridentea, Tromotriche, Tweedia, Tylophora, Tylophoropsis, Vailia, Vincetoxicopsis, Vincetoxicum, Voharanga, Vohemaria, White-Sloanea, Widgrenia, Woodia, Xysmalobium*<br>(7) Combretaceae | |
| Taxonomy. Subclass Dicotyledonae; Crassinucelli. Dahlgren's Superorder Myrtiflorae; Myrtales. Cronquist's Subclass Rosidae; Myrtales. APG (1998) Eudicot; core Eudicot; Rosid; Eurosid II; Myrtales. Species 600. Genera about 20; *Anogeissus, Buchenavia, Bucida, Calopyxis, Calycopteris, Combretum, Conocarpus, Dansiea, Guiera, Laguncularia, Lumnitzera, Macropteranthes, Melostemon, Pteleopsis, Quisqualis, Strephonema, Terminalia, Terminaliopsis, Thiloa*<br>(8) Amaranthaceae | alkaloids, arthroquinones, proanthocyanidins, cyanidins, flavonols, kaempferol, quercetin, myricetin, ellagic acid, aluminium, sucrose and oligosaccharides |
| Taxonomy. Subclass Dicotyledonae; Crassinucelli. Dahlgren's Superorder Caryophylliflorae; Caryophyllales. Cronquist's Subclass Caryophyllidae; Caryophyllales. APG (1998) Eudicot; core Eudicot; neither Rosid nor Asterid; Caryophyllales. Species 850. Genera 74; *Achyranthes, Achyropsis, Aerva, Allmania, Alternanthera, Amaranthus, Arthraerua, Blutaparon, Bosea, Brayulinea, Calicorema, Celosia, Centema, Centemopsis, Centrostachys, Chamissoa, Charpentiera, Chionothrix, Cyathula, Dasysphaera, Dasysphaera, Deeringia, Digera, Eriostylos, Froelichia, Gomphrena, Gossypianthus, Guilleminea, Hebanthe, Hemichroa (~Chenopodiaceae), Henonia, Herbstia, Hermbstaedtia, Indobanalia, Irenella, Iresine, Kyphocarpa, Lagrezia, Leucosphaera, Lithophila, Lopriorea, Marcelliopsis, Mechowia, Nelsia, Neocentema, Nothosaerva, Nototrichium, Nyssanthes, Pandiaka, Pfaffia, Philoxerus, Pleuropetalum, Pleuropterantha, Polyrhabda, Pseudogomphrena, Pseudoplantago, Pseudosericocoma, Psilotrichopsis, Psilotrichum, Ptilotus, Pupalia, Quaternella, Rosifax, Saltia, Sericocoma, Sericocomopsis, Sericorema, Sericostachys, Siamosia, Stilbanthus, Tidestromia, Trichuriella, Volkensinia, Woehleria, Xerosipho*<br>(9) Araceae | Cyanogenics, alkaloids, flavonols, quercetin, ellagic acid, betalains, saponins, sapogenins, oxalates |
| Taxonomy. Subclass Monocotyledonae. Superorder Ariflorae; Arales. APG (1998) Monocot; non-commelinoid; Alismatales. Species 2000. Genera 106; *Aglaodorum,* | Cyanogenics, cynogenic constituents tyrosine-derived, alkaloids, proanthocyanidins, |

TABLE I-continued

| PLANT | COMPOUNDS |
|---|---|
| *Aglaonema, Alloschemone, Alocasia, Ambrosina, Amorphophallus, Amydrium, Anadendrum, Anaphyllopsis, Anaphyllum, Anchomanes, Anthurium, Anubias, Aridarum, Ariopsis, Arisaema, Arisarum, Arophyton, Arum, Asterostigma, Biarum, Bognera, Bucephalandra, Caladium, Calla, Callopsis, Carlephyton, Cercestis, Chlorospatha, Colletogyne, Colocasia, Cryptocoryne, Culcasia, Cyrtosperma, Dieffenbachia, Dracontioides, Dracontium, Dracunculus, Eminium, Epipremnum, Filarum, Furtodoa, Gearum, Gonatanthus, Gonatopus, Gorgonidium, Gymnostachys, Hapaline, Helicodiceros, Heteroaridarum, Heteropsis, Holochlamys, Homalomena, Hottarum, Jasarum, Lagenandra, Lasia, Lasimorpha, Lysichiton, Mangonia, Monstera, Montrichardia, Nephthytis, Orontium, Pedicellarum, Peltandra, Philodendron, Phymatarum, Pinellia, Piptospatha, Pistia, Podolasia, Pothoidium, Pothos, Protarum, Pseudodracontium, Pseudohydrosme, Pycnospatha, Remusatia, Raphidophora, Rhodospatha, Sauromatum, Scaphispatha, Schismatoglottis, Scindapsus, Spathantheum, Spathicarpa, Spathiphyllum, Stenospermation, Steudnera, Stylochaeton, Symplocarpus, Synandrospadix, Syngonium, Taccarum, Theriophonum, Typhonium, Typhonodorum, Ulearum, Urospatha, Urospathella, Xanthosoma, Zamiculcas, Zantedeschia, Zomicarpa, Zomicarpella*<br>(10) Cyperaceae | cyanidin, flavonols, kaempferol, quercetin, and quercetin |
| Taxonomy. Subclass Monocotyledonae. Superorder Commeliniflorae; Cyperales. APG (1998) Monocot; Commelinoid group; Poales. Species about 5000. Genera about 120; *Abildgaardia, Acriulus, Actinoschoenus, Afrotrilepis, Alinula, Androtrichum, Anosporum, Arthrostylis, Ascolepis, Ascopholis, Baeothryon, Baumea, Becquerelia, Bisboeckelera, Blysmopsis, Blysmus, Bolboschoenus, Bulbostylis, Calyptrocarya, Capitularina, Carex, Carpha, Caustis, Cephalocarpus, Chorizandra, Chrysitrix, Cladium, Coleochloa, Costularia, Courtoisina, Crosslandia, Cyathochaeta, Cyathocoma, Cymophyllus, Cyperus, Desmoschoenus, Didymiandrum, Diplacrum, Diplasia, Dulichium, Egleria, Eleocharis, Eleogiton, Epischoenus, Eriophoropsis, Eriophorum, Erioscirpus, Evandra, Everardia, Exocarya, Exochogyne, Ficinia, Fimbristylis, Fuirena, Gahnia, Gymnoschoenus, Hellmuthia, Hemicarpha, Hymenochaeta, Hypolytrum, Isolepis, Kobresia, Kyllinga, Kyllingiella, Lagenocarpus, Lepidosperma, Lepironia, Lipocarpha, Lophoschoenus, Machaerina, Mapania, Mapaniopsis, Mariscus, Mesomelaena, Microdracoides, Micropapyrus, Monandrus, Morelotia, Neesenbeckia, Nemum, Nelmesia, Oreobolopsis, Oreobolus, Oxycaryum, Paramapania, Phylloscirpus, Pleurostachys, Principina, Pseudoschoenus, Ptilanthelium, Pycreus, Queenslandiella, Reedia, Remirea, Rhynchocladium, Rhynchospora, Rikliella, Schoenoplectus, Schoenoxiphium, Schoenoides, Schoenus, Scirpodendron, Scirpoides, Scirpus, Scleria, Sphaerocyperus, Sumatroscirpus, Syntrinema, Tetraria, Tetrariopsis, Thoracostachyum, Torulinium, Trachystylis, Trianoptiles, Trichoschoenus, Tricostularia, Trilepis, Tylocarya, Uncinia, Vesicarex, Volkiella, Websteria.*<br>(11) Anacardiaceae | Alkaloids, proanthocyanidins, cyanidins, delphinidins flavonols, quercetins, aluminium |
| Taxonomy. Subclass Dicotyledonae; Crassinucelli. Dahlgren's Superorder Rutiflorae; Sapindales. Cronquist's Subclass Rosidae; Sapindales. APG (1998) Eudicot; core Eudicot; Rosid; Eurosid II; Sapindales. Species 600. Genera about 70; *Actinocheita, Anacardium, Androtium, Antrocaryon, Apterokarpos, Astronium, Baronia, Bonetiella, Bouea, Buchanania, Campnosperma, Cardenasiodendron, Choerospondias, Comocladia, Cotinus, Cyrtocarpa, Dracontomelon, Drimycarpus, Ebandoua, Euleria, Euroschinus, Faguetia, Fegimanra, Gluta, Haematostaphis, Haplorhus, Harpephyllum, Heeria, Holigarna, Koordersiodendron, Lannea, Laurophyllus, Lithrea, Loxopterigium, Loxostylis, Mangifera, Mauria, Melanochyla, Metopium, Micronychia, Montagueia, Mosquitoxylum, Nothopegia, Ochoterenaea, Operculicarya, Ozoroa, Pachycormus, Parishia, Pegia, Pentaspadon,* | Alkaloids, iridoids, proanthocyanidins, delphinidins, cyanidins, flavonols, eg. kaempferol, quercetin, and myricetin; saponins/sapogenins sugars as sucrose, oligosaccharides or sugar alcohols |

TABLE I-continued

| PLANT | COMPOUNDS |
|---|---|
| *Pleiogynium, Poupartia, Protorhus, Pseudoprotorhus, Pseudosmodingium, Pseudospondias, Rhodosphaera, Rhus, Schinopsis, Schinus, Sclerocarya, Semecarpus, Smodingium, Solenocarpus, Sorindeia, Spondias, Swintonia, Tapirira, Thyrsodium, Toxicodendron, Trichoscypha.*<br>(12) Bignoniaceae | |
| Taxonomy. Subclass Dicotyledonae; Tenuinucelli. Dahlgren's Superorder Lamiiflorae; Scrophulariales. Cronquist's Subclass Asteridae; Scrophulariales. APG (1998) Eudicot; core Eudicot; Asterid; Euasterid I; Lamiales. Species 650. Genera 110; *Adenocalymna, Amphilophium, Amphitecna, Anemopaegma, Argylia, Arrabidaea, Astianthus, Barnettia, Bignonia, Callichlamys, Campsidium, Campsis, Catalpa, Catophractes, Ceratophytum, Chilopsis, Clytostoma, Colea, Crescentia, Cuspidaria, Cybistax, Delostoma, Deplanchea, Digomphia, Dinklageodoxa, Distictella, Distictis, Dolichandra, Dolichandrone, Eccremocarpus, Ekmanianthe, Fernandoa, Fridericia, Gardnerodoxa, Glaziova, Godmania, Haplolophium, Haplophragma, Heterophragma, Hieris, Incarvillea, Jacaranda, Kigelia, Lamiodendron, Leucocalantha, Lundia, Macfadyena, Macranthisiphon, Manaosella, Mansoa, Markhamia, Martinella, Melloa, Memora, Millingtonia, Mussatia, Neojobertia, Neosepicaea, Newbouldia, Nyctcalos, Ophiocolea, Oroxylum, Pajanelia, Pandorea, Parabiognonia, Paragonia, Paratecoma, Parmentiera, Pauldopia, Perianthomega, Periarrabidaea, Perichlaena, Phryganocydia, Phyllarthron, Phylloctenium, Piriadacus, Pithecoctenium, Pleionotoma, Podranea, Potamoganos, Pseudocatalpa, Pyrostegia, Radermachera, Rhigozum, Rhodocolea, Roentgenia, Romeroa, Saritaea, Sparattosperma, Spathicalyx, Spathodea, Sphingiphila, Spirotecoma, Stereospermum, Stizophyllum, Tabebuia, Tanaecium, Tecoma, Tecomanthe, Tecomella, Tourrettia, Tynanthus, Urbanolophium, Xylophragma, Zeyheria.*<br>For discussion of classificatory problems posed by *Scrophulariaceae*, impinging on *Bignoniaceae, Buddlejaceae, Callitrichaceae, Plantaginaceae, Hippuridaceae, Lentibulariaceae*, and *Hydrostachydaceae*, and such problem genera as *Paulownia* and *Schlegelia*, see Olmstead and Reeves (1995).<br>(13) Bombacaceae | Alkaloids, iridoids arthroquinones, shikimic acid, verbascosides, cornosides, flavonols, quercetins, ursolic acid, saponins, sapogenins oligosaccharides, sucrose, sugar |
| Taxonomy. Subclass Dicotyledonae; Crassinucelli. Dahlgren's Superorder Malviflorae; Malvales. Cronquist's Subclass Dilleniidae; Malvales. APG (1998) Eudicot; core Eudicot; Rosid; Eurosid II; Malvales. Species 180. Genera 30; *Adansonia, Aguiaria, Bernoullia, Bombacopsis, Bombax, Catostemma, Cavanillesia, Ceiba, Chorisia, Coelostegia, Cullenia, Durio, Eriotheca, Gyranthera, Huberodendron, Kostermansia, Matisia, Neesia, Neobuchia, Ochroma, Pachira, Patinoa, Phragmotheca, Pseudobombax, Quararibea, Rhodognaphalon, Rhodagnaphalopsis, Scleronema, Septotheca, Spirotheca. Malvaceae, Bombacaceae, Sterculiaceae* and *Tiliaceae*<br>(14) Anacardiaceae | Alkaloids, proanthocyanidins, cyanidins, flavonols e.g. kaempferol and quercetin; sucrose |
| Taxonomy. Subclass Dicotyledonae; Crassinucelli. Dahlgren's Superorder Rutiflorae; Sapindales. Cronquist's Subclass Rosidae; Sapindales. APG (1998) Eudicot; core Eudicot; Rosid; Eurosid II; Sapindales. Species 600. Genera about 70; *Actinocheita, Anacardium, Androtium, Antrocaryon, Apterokarpos, Astronium, Baronia, Bonetiella, Bouea, Buchanania, Campnosperma, Cardenasiodendron, Choerospondias, Comocladia, Cotinus, Cyrtocarpa, Dracontomelon, Drimycarpus, Ebandoua, Euleria, Euroschinus, Faguetia, Fegimanra, Gluta, Haematostaphis, Haplorhus, Harpephyllum, Heeria, Holigarna, Koordersiodendron, Lannea, Laurophyllus, Lithrea, Loxopterigium, Loxostylis, Mangifera, Mauria, Melanochyla, Metopium, Micronychia, Montagueia, Mosquitoxylum, Nothopegia, Ochoterenaea, Operculicarya, Ozoroa, Pachycormus, Parishia, Pegia, Pentaspadon, Pleiogynium, Poupartia, Protorhus, Pseudoprotorhus, Pseudosmodingium, Pseudospondias, Rhodosphaera, Rhus,* | Alkaloids, arthroquinones, proanthocyanidins, delphinidin, cyanidin, flavonols, kaempferol, quercetin, myricetin, ellagic acid, saponins, sapogenins, sucrose, oligosaccharides, sugar alcohols |

TABLE I-continued

| PLANT | COMPOUNDS |
| --- | --- |
| *Schinopsis, Schinus, Sclerocarya, Semecarpus, Sorindeia Smodingium, Solenocarpus, , Spondias, Swintonia, Tapirira, Thyrsodium, Toxicodendron, Trichoscypha.* (15) Caricaceae | |
| Taxonomy. Subclass Dicotyledonae; Crassinucelli. Dahlgren's Superorder Violiflorae; Violales. Cronquist's Subclass Dilleniidae; Violales. APG (1998) Eudicot; core Eudicot; Rosid; Eurosid II; Brassicales. Species 55. Genera 4; *Carica, Cylicomorpha, Jacaratia, Jarilla.* (16) Cynosuraceae | mustard-oils, alkaloids, saponins/sapogenins |
| *Strophantus* | |

Prior to the administration to a patient an extract or a mixture of extracts are typically diluted by combination with a pharmecologically compatible solvent, e.g., ethanol or water to produce a therapeutic solution. Typically the amount or concentration of the extract or mixed extracts in the therapeutic solution ranges from 0.0001 to 10.0 weight percent of the total weight of the solution. Of course, the extract or mixture of extracts is present in a therapeutically effective amount, that is, an amount such that the extract or mixture of extracts can be administered in a therapeutically effective amount through conventional oral, nasal, aerosol, topical, intravenous, peritoneal, etc. means.

The term "amount" as used herein refers to a quantity or to a concentration, as appropriate to the context. The amount of extract(s) that constitutes a therapeutically effective amount varies according to factors such as the potency of the extract(s) the route of administration of the formulation, and the mechanical system used to administer the formulation. A therapeutically effective amount of a particular extract or mixture of extracts can be selected by those of ordinary skill in the art with due consideration of such factors. Generally a therapeutically effective amount will be from about 0.005 parts weight to about 2 parts by weight based on 100 parts by weight of the therapeutic solution, or if in solid form, e.g., tablet or capsule, 0.001 to 10 parts by weight of the weight of the tablet or capsule.

For oral administration, either solid or fluid unit dosage forms can be prepared. For preparing solid compositions such as tablets, the extract or extract mixture is mixed into formulations with conventional ingredients, such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the extract or extract mixture with an inert pharmaceutical diluent and filling the mixture into a hard gelatin capsule of appropriate size. Soft gelatin capsules are prepared by machine encapsulation of a slurry of the extract or extract mixture with an acceptable vegetable oil, light liquid petrolatum or other inert oil.

Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill. Usually, the therapeutic extract or extract mixture is prepared in an aqueous solution in a concentration of from about 1 to about 100 mg/ml. More typically, the concentration is from about 10 to about 20 mg/ml. The formulation, which is sterile, is suitable for various parenteral routes including intra-dermal, intraarticular, intra-muscular, intravascular, and subcutaneous.

In addition to the therapeutic extract or extract mixture the compositions may include, depending on the formulation desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline solutions, Ringer's solution, dextrose solution, and Hank's solution. In addition, the pharmaceutical composition or formulation may include additives such as other carriers; adjuvants; or nontoxic, non-therapeutic, nonimmunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives and excipients are those amounts which are effective to obtain a pharmaceutically acceptable formulation in terms of solubility, biological activity, etc.

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals.

Examples of unit dosage forms are tablets, capsules, pills, powder packets, wafers, suppositories, granules, cachets, teaspoonfuls, dropperfuls, ampoules, vials, aerosols with metered discharges, segregated multiples of any of the foregoing, and other forms as herein described.

Thus, a formulation of the invention includes a therapeutic extract(s) which may be formulated with conventional, pharmaceutically acceptable, vehicles for topical, oral or parenteral administration. Formulations may also include small amounts of adjuvants such as buffers and preservatives to maintain isotonicity, physiological and pH stability. Means of preparation, formulation and administration are known to those of skill. See generally Remington's Pharmaceutical Science $15^{th}$ ed., Mack Publishing Co., Easton, Pa. (1980).

Slow or extended-release delivery systems, including any of a number of biopolymers (biological-based systems), systems employing liposomes, and polymeric delivery systems, can be utilized with the extracts described herein to provide a continuous or longterm source of therapeutic compound. Such slow release systems are applicable to formulations for topical, ophthalmic, oral, and parenteral use.

Delivery of the inventive therapeutic extractor extract mixture is usually by oral administration as a solution. However, where necessary, therapy, e.g., intra-dermal, intra-articular, intramuscular or intravenous, is also employed.

As previously indicated, the resultant medicament extract e.g., from a single plant or a mixture of any of the aforementioned plants, has been found to be effective in treating AIDS but also in treating associated conditions related to AIDS. Such associated conditions include recurrent and persistent fever, chronic diarrhea, dermatitis, generalized lymphodenpathy, persistent cough, general pain, tuberculosis, and amenorrhea.

EXAMPLES

1. About 105 patients suffering from AIDS were treated with mixtures of plant extracts, obtained as above described as approximately 10% weight percent therapeutic solutions with the following results as reported in TABLE II, below.

II. Treatment of HIV Patients for AIDS Related Ailments

A total of 300 patients presenting moderate to advanced stages of AIDS, particularly with respect to debilitating ailments, including persistent fever, chronic diarrhea, dermatitis, generalized lymphodenapathy, persistent cough, general pain, tuberculosis and amenorrhea, were treated with an extract mixture solution of the invention. The mixture comprised Anoceae (10 to 20 weight percent), Anarcadiaceae (15-20 weight percent), Araceae (15 to 20 weight percent) Bombacaceae (20 weight percent), Caricaceae (15 to 20 weight percent), and Combretaceae (3 to 10 weight percent). The mixture was then diluted with water to give about 10 weight percent extract solution. The solution was administered to each patient at a dose of 3 tablespoons three times per day.

All treated patients in this group of studies had none of the debilitating symptoms in the time periods indicated in TABLE III, below:

TABLE III

| Symptom | Approximate Recovery Time (Average) |
|---|---|
| R/P Fever | 1 Week |
| Chronic Diarrhea | 1 Week |
| Dermatitis | 3 Weeks |
| Generalizied Lymphodenpathy | 4 Weeks |
| Cough | 2 Weeks |
| General Pain | 4 Weeks |
| Tuberculosis | 12 Weeks |
| Amenorrhea | 1 Week |

TABLE II

Combinations of Plant Extract Medicaments for Treatment of AIDS Related Ailments

| Stage of AIDS Disease | Typical Symptoms | Mixture of Plant Extract Used |
|---|---|---|
| Stage 1: Critically ill - non-ambulatory patients 3–6 months duration of treatment (Complete 90 to 98%) | Significant weight loss Frequent and recurrent Fever Chronic Diarrhea Dermatitis Generalized Lymphodenpathy, Cough General Pain Pneumonia Kaposi's sarcoma Herpes zoster Tuberculosis Amenorrhea | Apocynaceae (17 weight percent) Annonaceae (10 weight percent) Dichapetalaceae (14 weight percent) Annoceae (17 weight percent) Cynocynaceae (21 weight percent) Asclepiadaceae (14 weight percent) Combretaceae (7 weight percent) Diluted with to give a 0.5 to 25 weight percent extracts solution |
| Stage 2: Moderately ill - after going through stage 1 treatment program 3–6 months duration of treatment (Complete 95%) | Lack of appetite Immune dysfunction | Apoocynaceae (15 weight percent) Amaranthaceae (17 weight percent) Aroceae (17 weight percent) Cyperaceae (17 weight percent) Anacardiaceae (17 weight percent) bignoniaceae (17 weight percent) Diluted with water to give a 0.5 to 25% weight percent extract solution |
| Stage 3: Relatively ill but ambulatory with good vitals after stage 2 program 3–6 months duration of treatment | Restoration of immune protection | Anoceae (17 weight percent) Anarcadiaceae (20 weight percent) Aroceae (20 weight percent) Bombacaceae (20 weight percent) Caricaceae (17 weight percent) Combretaceae (6 weight percent) Diluted with water to give a 0.5 to 25 weight percent extract solution |

ORAL

DOSAGES: Adults 3 tablespoonsfull 3 times daily
Pediatric: 2 teaspoonful 3 times daily

We claim:

1. A composition for treating symptoms of AIDS patients, comprising a mixture of extracts from the following plants:

*Alstonia boonei, Cleistopholis patens, Dichapetalum madagascariense, Uvariastrum pierreanum, Strophanthus gratus, Gongronema latifolium* and *Combretum racemosum,* wherein the symptoms of AIDS are at least one or more selected from the group consisting of: recurrent fever, chronic diarrhea, general body pain, persistent cough, dermatitis, and weight loss.

2. The composition according to claim 1, further comprising one or more compound(s) derived from one or more of the foregoing plants, said compounds selected from the group consisting of: a glyceryl, a saponin, an alkaloid, a protein, a fat, and a sugar.

3. The composition according to claim 1, wherein (a) *Alstonia boonei* is present in the composition in an amount of 17 weight percent;

(b) *Cleistopholis patens* is present in the composition in an amount of 10 weight percent;

(c) *Dichapetalum madagascariense* is present in the composition in an amount of 14 weight percent;

(d) *Uvariastrum pierreanum* is present in the composition in an amount of 17 weight percent;

(e) *Strophanthus gratus* is present in the composition in an amount of 21 weight percent;

(f) *Gongronema latifolium* is present in the composition in an amount of 14 weight percent; and (g) *Combretum racemosum* is present in the composition in an amount of 7 weight percent;

wherein the mixture of extracts from (a), (b) or (c) of claim 1 is further diluted with water to give a 0.5 to 25 weight percent extracts solution.

* * * * *

UNITED STATES PATENT AND TRADEMARK OFFICE
CERTIFICATE OF CORRECTION

PATENT NO. : 7,749,544 B2
APPLICATION NO. : 10/902993
DATED : July 6, 2010
INVENTOR(S) : William Asiedu It is certified that error appears in the above-identified patent and that said Letters Patent is hereby corrected as shown below:

Column 20, lines 13-14, in claim 3, "--wherein the mixture of extracts from (a), (b) or (c) of claim 1 is further diluted--" should be changed to "--wherein the mixture of extracts is further diluted--".

Signed and Sealed this

Tenth Day of August, 2010

David J. Kappos
*Director of the United States Patent and Trademark Office*